United States Patent [19]

Grossmann

[11] Patent Number: 4,469,485
[45] Date of Patent: Sep. 4, 1984

[54] USE OF THE 1:2 CHROMIUM COMPLEX OF 1-AMINO-2-(3', 5'-DINITRO-2'-HYDROXYPHENYLAZO)-4-SULFONAPHTHALENE AND ALKALI METAL SALTS THEREOF FOR DYEING POLYAMIDES AND OXIDE LAYERS ON ALUMINUM AND ALUMINUM ALLOYS

[75] Inventor: Hans Grossmann, Oberwil, Switzerland

[73] Assignee: Sandoz Ltd., Basel, Switzerland

[21] Appl. No.: 524,993

[22] Filed: Aug. 22, 1983

Related U.S. Application Data

[60] Division of Ser. No. 964,698, Nov. 29, 1978, Pat. No. 4,416,816, which is a continuation-in-part of Ser. No. 373,630, Jun. 26, 1973, abandoned.

[30] Foreign Application Priority Data

Jun. 28, 1972 [CH] Switzerland ............ 9676/72

[51] Int. Cl.³ .................. C07C 143/38; C09B 45/16; D06P 3/04
[52] U.S. Cl. ......................... 8/522; 8/683; 8/685; 8/917; 8/924; 260/151; 260/208
[58] Field of Search ............ 8/522, 685, 683

[56] References Cited

U.S. PATENT DOCUMENTS

| | | | |
|---|---|---|---|
| 1,626,167 | 4/1927 | Straub | 260/151 |
| 2,030,236 | 2/1936 | Anderau | 148/6.1 |
| 3,019,143 | 1/1962 | Dessauer | 148/6.1 |
| 3,079,309 | 2/1963 | Wainer | 8/522 |
| 3,172,786 | 3/1965 | Kirby et al. | 8/522 |
| 3,291,651 | 12/1966 | Brassel | 148/6.1 |
| 4,416,816 | 11/1983 | Grossmann | 260/151 |

FOREIGN PATENT DOCUMENTS 907253 10/1962 United Kingdom .

Primary Examiner—A. Lionel Clingman
Attorney, Agent, or Firm—Gerald D. Sharkin; Richard E. Vila; Melvyn M. Kassenoff

[57] ABSTRACT

Disclosed are the 1:2 chromium complex of the formula

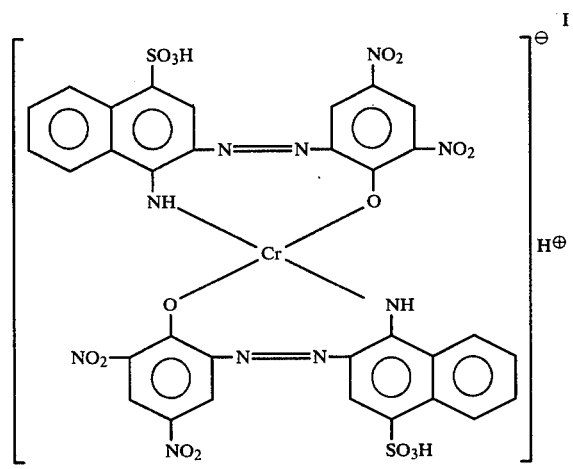

and the alkali metal salts thereof which are useful for the coloration of oxide layers produced on aluminum and alloys thereof and for dyeing natural and synthetic polyamides.

17 Claims, No Drawings

USE OF THE 1:2 CHROMIUM COMPLEX OF 1-AMINO-2-(3',5'-DINITRO-2'-HYDROXYPHENYLAZO)-4-SULFONAPHTHALENE AND ALKALI METAL SALTS THEREOF FOR DYEING POLYAMIDES AND OXIDE LAYERS ON ALUMINUM AND ALUMINUM ALLOYS

This application is a division of application Ser. No. 964,698, filed Nov. 29, 1978 and now U.S. Pat. No. 4,416,816 issued Nov. 22, 1983, which is a continuation-in-part of application Ser. No. 373,630, filed June 26, 1973 and now abandoned.

The present invention relates to anionic 1:1-chromium complexes, their production and use as dyes.

The present invention provides the 1:2 chromium complex of formula I,

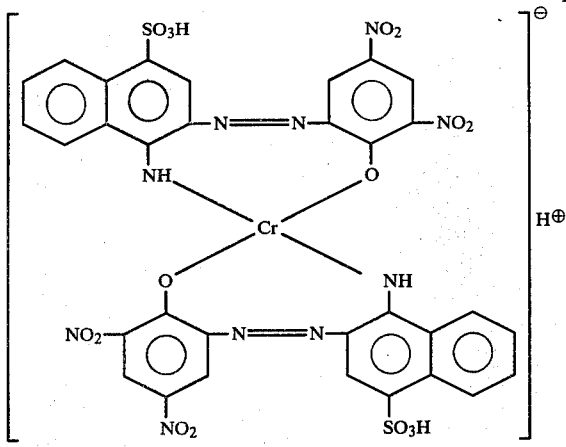

and the alkali metal salts thereof.

The present invention further provides a process for the production of the chromium complex of formula I characterized by treating a compound of formula II,

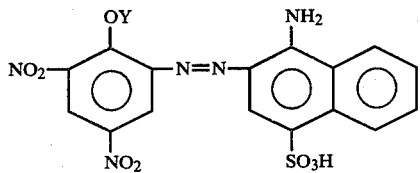

wherein Y is hydrogen, $C_{1-4}$ alkyl or acyl, with a chromium donor.

Suitable chromium donors include, for example, the chromic salts, such as chromic fluoride, chromic chloride, chromic sulphate, chrome alum, chromium-ammonium sulphate, chromic formate and chromic acetate, and also complex salts of the $Cr^{+++}$ ion, such as chromic oxalate, chromic tartrate, chromic lactate, chromic salicylate, chromic oxide and chromic hydroxide. Salts of hexavalent chromium, in which the chromium is in the anionic radical, such as potassium and sodium chromates and dichromates, are also suitable. In the latter case, it is preferred to carry out the chromatisation in an alkaline aqueous medium in the presence of a reducing agent, such as furfural or glucose.

The quantity of the chromium donor is selected in such a way that at least one atom of chromium is available for two molecules of the monoazo compound of formula II. In general, it is recommended to use less than two atoms of chromium per two molecules of the compound of formula II.

Chromatisation is preferably carried out in an organic solvent miscible with water, such as formamide, glycerol or ethylene glycol, in water or in a mixture of the above solvents with water. It is recommended that the reaction be carried out at a pH greater than 4, i.e. under slightly acid, neutral or alkaline conditions. The conversion of the monoazo compound to the chromium complex is preferably carried out at a temperature within the range of 80° to 135° C., or at the boiling point of the reaction mixture, either under atmospheric or super atmospheric pressure. The reaction may be assisted by the addition of substances favourable to complex formation, such as oxalic and tartaric acids, or substances exerting an influence on the pH.

As will be appreciated, during complexing of compounds of formula II wherein Y is $C_{1-4}$ alkyl or acyl, such groups are split off during the reaction.

It is also possible to carry out chromatisation in two stages, as in processes of the prior art, in that the compound of formula II is treated with a chromium donor in such a manner that the reaction product contains one atom of chromium per molecule of this compound, after which one molecule of this reaction product, i.e. a 1:1 chromium complex, is made to react further with one molecule of the compound of formula II.

Separation of the final product is carried out in a conventional manner. For example, solutions of the product in organic solvents are diluted with water; the product itself may then be precipitated from the aqueous solution by cooling, possibly with the addition of salts. After this, the product is separated by filtration, followed by drying and grinding to a powder, if desired.

The compound of formula II can be obtained by diazotising 1-amino-2-hydroxy-3,5-dinitrobenzene, for example by means of sodium nitrite and hydrochloric acid in an aqueous solution, followed by coupling the resulting diazonium compound with 1-aminonaphthalene-4-sulphonic acidic in a neutral or slightly acid medium. Chromatisation of the compound of formula II by means of a chromium donor may be carried out in the coupling mixture. However, for practical reasons it is advisable to separate the compound of formula II by means of filtration, if necessary after the addition of salt, and then to treat the filter cake (without drying) with the chromium donor. It is also possible, however, to start with the compound of formula II in dried form or after purification by recrystallisation.

By the term "acyl" as used herein is understood the residue which results from removing a hydroxyl group from an acid or hypothetical acid and is understood to include radicals of the formulae

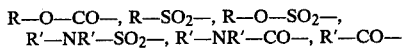

and wherein

R is an alkyl radical of 1 to 4 carbon atoms or a phenyl radical, and

R' is hydrogen, an alkyl radical of 1 to 4 carbon atoms or a phenyl radical.

The complexes of formula I are readily soluble in polar solvents such as ethylene glycol and formamide, and particularly in water, and are suitable for dyeing or printing various materials, such as natural and synthetic polyamides, for example wool, nylon and leather. The complexes of formula I are also particularly suitable for dyeing artificially produced oxide layers on the surface of metallic aluminum, i.e. layers produced by chemical or preferably anodising processes, preferably in aqueous solutions. Oxide layers dyed with a complex of formula I are characterized by good resistance to fading and particularly by the quality of their neutral grey colour.

By oxide layers produced by anodising processes is meant porous layers of aluminum oxide adhering firmly to the base metal, such as those produced by electrochemical treatment of the aluminum surface in an electrolyte containing water and a suitable acid, using direct current with the aluminum workpiece forming the anode. By the expression "neutral grey colour" is meant anthracite greys of the kind produced naturally by the anodising process described in more detail below.

In the field of surface treatments for aluminum, coloured oxide layers produced by anodisation play an important part owing to their exceptional resistance to mechanical damage and corrosion and also their highly decorative effects. In order to produce coloured oxide layers of the type defined, several basically distinct processes are available.

In a single-stage process, known as anodisation with self-coloration ("Integral Color Anodizing" or "Anodisation autocolorante") special aluminum alloys are used, and generally special organic acids as the electrolyte. Such processes are characterized in that the oxide layer is formed and coloured at the same time during the anodising process, whereby the colour is produced by the chemical or physical conversion and deposition of alloy constituents in the aluminum oxide layer. Consequently, the colour is generally dependent on the composition of the aluminum alloy used as a base.

In a two-stage process, a preferably colourless and transparent oxide layer is first produced by anodisation. Subsequently, colouring matter is introduced into the pores in the oxide layer, a distinction being drawn between electrolytic and adsorbtive deposition of the said colouring matter.

In the first case, namely that of coloration by the electrolytic deposition of metallic salts, the anodised aluminum is immersed in an aqueous solution which, in addition to an acid, contains special salts of heavy metals such as nickel and copper, the said metallic salts being deposited and converted by the passage of an alternating current in the form of coloured metals or metallic compounds.

In the second case, namely that of coloration by adsorption, the anodised aluminum is treated with a solution preferably containing an organic dyestuff. Aqueous solutions of anionic dyestuffs have been found to be particularly suitable for this purpose. In this case, coloration occurs by a purely adsorbtive process without the use of an electric current.

Adsorbtive coloration processes are superior to electrolytic processes in several respects. Since the coloration is on the one hand independent of the composition and state of the alloy and on the other of an electric current, the adsorbtive process requires less storage space, apparatus and supervision. Also, the slight differences in alloy quality and current distribution which are unavoidable in practice can have no adverse effect. Coloration produced by the adsorbtive process is hence characterized by a greater degree of evenness and reproducibility. Owing to its simplicity, adsorbtive coloration is unrivalled from the economic point of view.

However, it is sometimes necessary to use the electrolytic coloration process since certain preferred colours cannot be produced in a satisfactory way by the adsorbtive method. For example, it is necessary to produce the particularly valuable neutral grey tones by means of a special form of the anodising process with integral coloration. The process known as anodising with integral grey coloration comprises anodising aluminum alloys with a silicon content exceeding the solubility limit, for example 3.5 to 8% silicon, in dilute sulphuric acid. The production of such alloys with uniform quality and their anodising involve particularly great difficulties, which have an adverse effect on both the economy of the method and the uniformity of the grey coloration produced.

In view of the above-mentioned drawbacks of this method, attempts have been made for a long time to find a way of producing neutral grey tones by adsorbtive means, although no satisfactory solution has been found in the prior art. It was in fact found possible to produce neutral grey tones by the simultaneous use of several organic dyestuffs. However, when organic dyestuffs are used, it is necessary on economic grounds to use the same bath for a prolonged period, which involves drawbacks which are very difficult to overcome when mixtures of different dyestuffs are being used. The different rates of impoverishment in the various colour components causes unwanted variations in the tone of the coloration, which are particularly noticeable with neutral grey colours. Deviations from the original colour tone cannot be very satisfactorily corrected by subsequent additions to the dyeing bath.

It has now been discovered quite unexpectedly that it is possible to colour artificially produced oxide layers on aluminum evenly in neutral grey tones ranging from light to very dark by treating the said oxide layers on aluminum with a solution of a complex of formula I.

The treatment occurs in accordance with methods known in the prior art. For example, a complex of formula I dissolved in water, an organic solvent such as a $C_{1-4}$ alcohol, acetone, ethylene glycol or a mixture thereof, may be applied to the anodised aluminum by means of brushing, swabbing, etc., or by spraying.

Also, for the purposes of graphical reproduction, the solution of a complex of formula I may be converted into a printable form by the addition of a viscosity improver and applied to the oxide layer by a generally used printing process, for example with a rubber stamp or by a silk-screen process. The best method, however, is by immersion of the anodised aluminum in an aqueous solution of a complex of formula I. By suitable masking of the oxidised surface layer it is possible with the immersion method to obtain partial and varied colour tones. The treatment may be carried out at normal temperatures, i.e. over the range between ambient temperature, e.g. about 25° C., and the boiling point. Temperatures between 55° and 65° C. are particularly favourable. The pH is so chosen that the oxide layer is either not attacked or only slightly attacked, i.e. dyeing is preferably carried out in the pH range of 4.5 to 6. Adjustment and maintenance of the pH may be achieved by the use of the usual acids and bases, such as sulphuric acid, acetic acid and sodium hydroxide solution. If required, other additives generally used to improve the coloration process, such as equalising additives, buffer reagents and organic solvents miscible with water may be used.

The dyestuff concentration and time of treatment may be varied over a wide range, according, among other things, to the required intensity of the grey tone, the thickness and structure of the oxide layer, as well as the other dyeing conditions. The preferred concentration range is from 0.01 to 10 grams/liter, more preferably 0.1 to 10 grams/liter. The preferred treatment time is from 1 to 30 minutes. A treatment time of 15 to 20 minutes is particularly suitable.

By aluminum is meant not only pure aluminum, but also those aluminum alloys which behave in a similar manner to the pure metal with regard to anodic oxidation, such as alloys of the type Al/Mg, Al/Si, Al/Mg/Si, Al/Zn/Mg, Al/Cu/Mg and Al/Zn/Mg/Cu. As electrolytes for the anodising process, chromic, oxalic and sulphuric acids can be used, among others, as well as mixtures of oxalic and sulphuric acids. Particularly valuable results can be obtained by the use of alloys and anodising processes which result in transparent, colourless oxide layers. The direct current sulphuric acid process has been found to be the most suitable anodising method. However, it is also possible to use alloys and anodising processes which produce integrally coloured oxide layers.

The process may also be carried out in such a manner that dyeing occurs at the same time as the anodic production of the oxide layer or so that the complex of formula I is actually produced in the dyeing bath.

The complexes of formula I are also suitable for the coloration of chemically produced oxide layers on aluminum, the so-called conversion layers as produced, for example, by the effect of baths containing the salts of chromic acid in acid or alkaline media.

After dyeing, the coloured oxide layer is processed in the usual manner. A particularly advantageous method is the sealing of the oxide layer by treatment with boiling water or steam, if necessary in the presence of a reagent which aids sealing and at the same time inhibits leaching out of the dyestuff, such as nickel or cobalt acetate.

In view of the large number of organic dyestuffs suitable for the coloration of anodised aluminum known in the prior art, it could in no way be foreseen that the complexes of formula I would enable neutral grey tones to be produced by the adsorptive method for the first time. This result is all the more surprising in view of the fact that the use of closely related chemical substances does not produce a grey coloration. For example, the use of the chromium complex of the monoazo dyestuff obtained from diazotized 1-amino-2-hydroxy-3,5-dinitrobenzene and 1-aminonaphthalene-5-sulphonic acid gives olive-green tones. If the chromium atom combined as a complex in the dyestuff of formula I is replaced by a cobalt atom, a black colour is produced on anodised aluminum, in accordance with Example 1 of Swiss Pat. No. 363,744. If the cobalt complex is used in low concentrations, olive-green tones are also produced. Neither are grey tones obtained with any of the other dyestuffs described in the said patent. If the chromium complex of the monoazo dyestuff obtained from diazotized 1-amino-2-hydroxy-3,5-dinitrobenzene and 1-aminonaphthalene-4-sulphonic acid, in which one chromium atom is combined as a complex with one molecule of the monoazo dyestuff, giving a 1:1 chromium complex, a grey-blue coloration is produced.

It will be appreciated that the complex of formula I may be used in alkali metal salt form, especially the sodium salt form.

The following Examples serve to further illustrate the invention. In the Examples all parts and percentages are by weight and the temperatures are given in degrees centigrade unless otherwise stated.

EXAMPLE 1

43.3 Parts of the monoazo dyestuff obtained from diazotized 1-amino-2-hydroxy-3,5-dinitrobenzene and 1-aminonaphthalene-4-sulphonic acid, 39 parts of an aqueous solution of chromium acetate containing 11.8% $Cr_2O_3$ and 400 parts of water are refluxed with stirring for 10 hours. During the reaction the pH of the chrome-complexing mixture is maintained at 5.0 by means of aqueous sodium hydroxide solution. After cooling to room temperature, the crystallized reaction product is separated by filtration, dried and powdered. In pure form, the 1:2 chrmium complex of the monoazo dyestuff is obtained as a dark-grey powder, soluble in sulphuric acid to give a blue-red solution and in water to give a grey solution. The dyestuff colours anodically oxidized aluminum to give a neutral gray tone particularly resistant to fading on exposure to light.

Alternatively, if instead of drying the product obtained after filtration, the filtercake is dissolved at room temperature in a mixture of 19 parts of crystalline sodium acetate, 27 parts water and 111 parts diethylene glycol monoethyl ether, 230 parts of a stable liquid, homogeneous dark grey dyestuff preparation are obtained. Such preparation does not crysallize after prolonged storage at 0° C. and gives a clear solution in a matter of seconds when added to water.

The liquid preparation gives dyeings on anodically oxidized aluminum which have the same properties as dyeings made with the pure dyestuff.

The chromium complex may also be obtained by reacting 48.3 parts of the 1:1 chromium complex of the compound of the formula

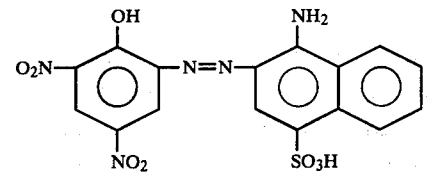

with an aqueous solution containing 43.3 parts of the monoazo dyestuff used above in 1000 parts of water at 70° C. and pH 4.8.

EXAMPLE 2

43.3 Parts of the monoazo dyestuff used in Example 1 are dissolved in 1000 parts of water at a pH of 8 to 9. The resulting solution is maintained at 100° C. for 1 hour, during which time 200 parts of an aqueous solution containing 8 parts of potassium dichromate and 18 parts of glucose is added dropwise. At the end of the reaction period, the chromium complex is precipitated by the addition of sodium chloride, separated and dried. The resulting substance is the chromium complex of the dyestuff described in Example 1.

APPLICATION EXAMPLE A

A degreased and stripped workpiece of pure aluminum is anodically oxidized for 30 minutes at a temperature of 18° to 20° C. with a direct current of density 1.5 amperes/$dm^2$ in an aqueous solution containing 20 parts of sulphuric acid and 1 part of aluminum sulphate per 100 parts.

After rinsing with water, the workpiece is immersed for a period of 15 minutes at a temperature of 60° C. in a solution containing 0.3 parts of the chromium complex produced in accordance with Example 1 in 1000 parts of deionised water whose pH is adjusted to 5 by means of acetic acid. The dyed workpiece is rinsed with water and then treated for 30 minutes at a temperature of 98° to 100° C. with deionised water. The result is a medium neutral grey coloration with a good resistance to fading on exposure to light.

If the said aluminum workpiece is printed prior to dyeing with a linseed-oil based printing ink by the offset process, and cleaned with xylene after the treatment with boiling water, a natural-coloured pattern on a grey background will be obtained.

If the workpiece is oxidised under otherwise identical conditions for a period of 60 minutes and then dyed in a solution containing 10 parts of the chromium complex per 1000 parts of water, a deep grey coloration of outstanding resistance to fading on exposure to light and weather conditions is obtained.

If the after-treatment is carried out under otherwise identical conditions with a buffered solution of the complex containing 3 parts nickel acetate in 1000 parts of water, a coloration of the same quality is obtained.

APPLICATION EXAMPLE B

10 Parts of the complex produced according to Example 1 are dissolved in 500 parts of water and stirred to form a highly viscous mixture with a solution comprising 400 parts of water and 100 parts of methylcellulose of a medium degree of polymerisation and 1.5 degrees substitution. The printing ink so obtained is applied by a silk-screen process to a dry oxidised aluminum sheet obtained by anodising an aluminum alloy of the type Al/Mg/Si(0.5) for 30 minutes in a solution of 100 parts chromic anhydride in 1000 parts of water at 53° C. and a current density of 1.2 amperes/dm². The printed aluminum alloy sheet is immersed in boiling water for 10 minutes and then rinsed throughly in cold water. A grey pattern on a pale greyish background is obtained.

What is claimed is:

1. A process for the coloration of a porous oxide layer on an aluminum or aluminum alloy substrate comprising contacting an aluminum or aluminum alloy substrate having a porous oxide layer thereon with a solution of a dye, said dye being the complex of the formula

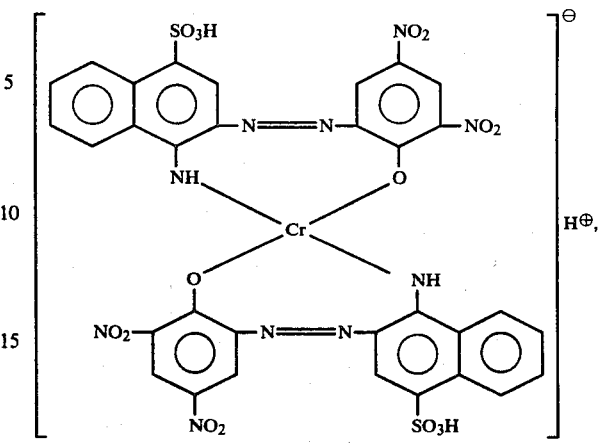

or an alkali metal salt thereof.

2. A process according to claim 1 wherein the solution is a solution of the dye in water, an alcohol having 1 to 4 carbon atoms, acetone or ethylene glycol, or a mixture thereof.

3. A process according to claim 2 wherein the solution is applied to the substrate to be colored by brushing, swabbing, spraying or printing or wherein the substrate is immersed in the solution.

4. A process according to claim 3 wherein the substrate is immersed in the solution.

5. A process according to claim 4 wherein the temperature of the solution is about 25° C. to the boiling point thereof.

6. A process according to claim 5 wherein the temperature of the solution is 55° C. to 65° C.

7. A process according to claim 4 wherein the substrate is immersed in the solution for 1 to 30 minutes.

8. A process according to claim 7 wherein the substrate is immersed in the solution for 15 to 20 minutes.

9. A process according to claim 4 comprising immersing an aluminum or aluminum alloy substrate having a porous oxide layer thereon in a solution of a dye in water, an alcohol having 1 to 4 carbon atoms, acetone or ethylene glycol, or a mixture thereof, for 1 to 30 minutes, said solution having a dye concentration of 0.1 to 10 grams per liter, a temperature of about 25° C. to the boiling point thereof and a pH of 4.5 to 6, said dye being the complex of the formula

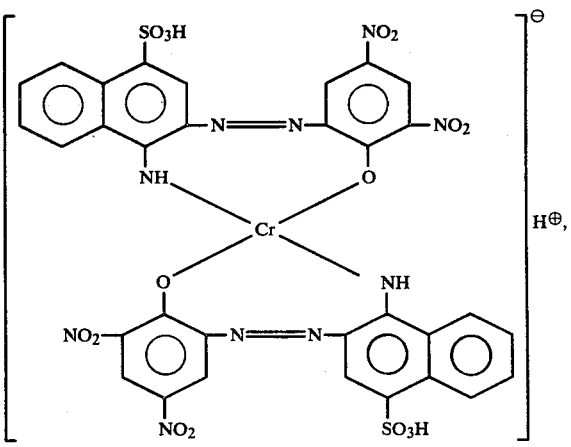

or an alkali metal salt thereof.

10. A process according to claim 9 wherein the dye is a sodium salt of the complex of the formula

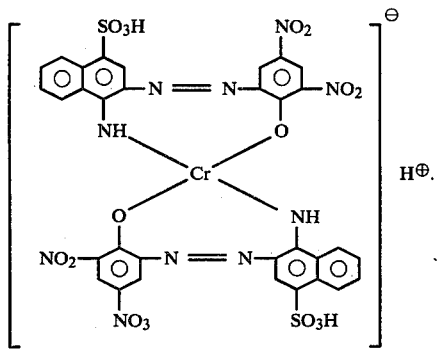

11. A process according to claim 1 wherein the pH of the solution is 4.5 to 6.

12. A process according to claim 1 wherein the dye concentration of the solution is 0.01 to 10 grams per liter.

13. A process according to claim 1 wherein the substrate is aluminum or an aluminum/magnesium, aluminum/silicon, aluminum/magnesium/silicon, aluminum/zinc/magnesium, aluminum/copper/magnesium or aluminum/zinc/magnesium/copper alloy.

14. A process according to claim 1 wherein the porous oxide layer on the substrate is an anodized oxide layer.

15. A process according to claim 1 wherein the dye is a sodium salt of the complex of the formula

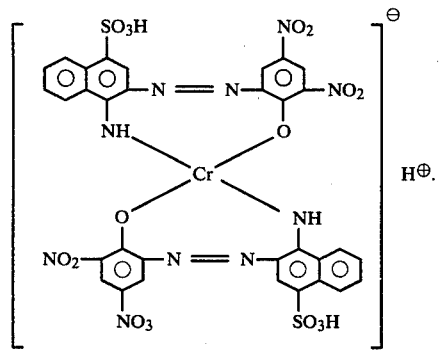

16. A process for dyeing a natural or synthetic polyamide substrate comprising treating a natural or synthetic polyamide substrate with a dye, said dye being the complex of the formula

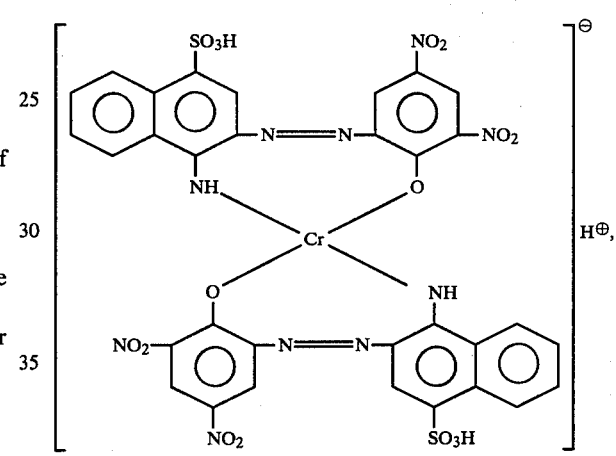

or an alkali metal salt thereof.

17. A process according to claim 16 wherein the dye is a sodium salt of the complex of the formula

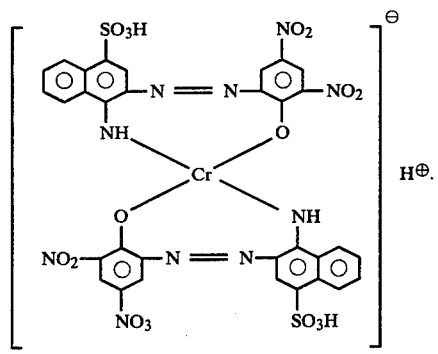

* * * * *